(12) United States Patent
Fischer et al.

(10) Patent No.: US 10,800,736 B2
(45) Date of Patent: Oct. 13, 2020

(54) PROCESS FOR PREPARING METHIONINE

(71) Applicant: Evonik Operations GmbH, Essen (DE)

(72) Inventors: Daniel Fischer, Midlothian, VA (US); Patrik Stenner, Hanau (DE); Sebastian Bernhardt, Aschaffenburg (DE); Harald Jakob, Hasselroth (DE)

(73) Assignee: Evonik Operations GmbH, Essen (DE)

( * ) Notice: Subject to any disclaimer, the term of this patent is extended or adjusted under 35 U.S.C. 154(b) by 0 days.

(21) Appl. No.: 16/605,090

(22) PCT Filed: May 9, 2018

(86) PCT No.: PCT/EP2018/061941
§ 371 (c)(1),
(2) Date: Oct. 14, 2019

(87) PCT Pub. No.: WO2018/215206
PCT Pub. Date: Nov. 29, 2018

(65) Prior Publication Data
US 2020/0157045 A1    May 21, 2020

(30) Foreign Application Priority Data
May 24, 2017    (EP) .................................... 17172737

(51) Int. Cl.
*C07C 319/20*    (2006.01)
*C07C 319/14*    (2006.01)
(Continued)

(52) U.S. Cl.
CPC .......... *C07C 319/20* (2013.01); *C07C 319/14* (2013.01); *C07C 319/28* (2013.01); *C07C 323/58* (2013.01)

(58) Field of Classification Search
None
See application file for complete search history.

(56) References Cited

U.S. PATENT DOCUMENTS

| 4,238,307 A | 12/1980 | Perry et al. |
| 4,454,012 A | 6/1984 | Bachot et al. |

(Continued)

FOREIGN PATENT DOCUMENTS

| CN | 105671587 | 6/2016 |
| CN | 106349131 | 1/2017 |

(Continued)

OTHER PUBLICATIONS

International Search Report dated Aug. 7, 2018 in PCT/EP2018/061941.

(Continued)

*Primary Examiner* — Amy C Bonaparte
(74) *Attorney, Agent, or Firm* — Grüneberg and Myers PLLC

(57) ABSTRACT

A process is used for preparing methionine. Specifically, the process includes the hydrolysis of 5-(2-methylmercaptoethyl)hydantoin (methionine hydantoin) in an alkaline process solution. Further, the by-products that include formate and other anions of organic acids containing 1 to 5 carbon atoms are removed by electrodialysis of the process solution.

7 Claims, 4 Drawing Sheets

(51) Int. Cl.
    *C07C 319/28*    (2006.01)
    *C07C 323/58*    (2006.01)

(56) References Cited

U.S. PATENT DOCUMENTS

| | | |
|---|---|---|
| 4,909,916 A | 3/1990 | Koberstein et al. |
| 5,770,769 A | 6/1998 | Geiger et al. |
| 9,023,284 B2 | 5/2015 | Hasselbach et al. |
| 9,403,764 B2 | 8/2016 | Hasselbach et al. |
| 2013/0231501 A1 | 9/2013 | Hasselbach et al. |
| 2015/0175535 A1 | 6/2015 | Hasselbach et al. |

FOREIGN PATENT DOCUMENTS

| | | | |
|---|---|---|---|
| CN | 106432020 | | 2/2017 |
| CN | 106748932 | * | 5/2017 |
| DE | 29 07 450 | | 9/1980 |
| DE | 36 03 986 | | 8/1987 |
| EP | 1 564 208 | | 5/2011 |
| WO | 2013/030068 | | 3/2013 |

OTHER PUBLICATIONS

Written Opinion dated Aug. 7, 2018 in PCT/EP2018/061941.
International Preliminary Report on Patentability dated Sep. 17, 2019 in PCT/EP2018/061941.
Strathmann et al., Chem.-Ing.-Tech. 56 (1984) No. 3, 214-220.

* cited by examiner

1: Anolyte
2: Process solution
3: Catholyte

Figure 4

PROCESS FOR PREPARING METHIONINE

This application is a National Stage entry under § 371 of International Application No. PCT/EP2018/061941, filed on May 9, 2018, and which claims the benefit of European Application No. 17172737.3, filed on May 24, 2017.

BACKGROUND OF THE INVENTION

Field of the Invention

The present invention relates to a process for preparing methionine comprising the hydrolysis of 5-(2-methylmercaptoethyl)hydantoin (methionine hydantoin) in an alkaline process solution in which by-products comprising formate and other anions of organic acids comprising 1 to 5 carbon atoms are removed from the process solution by electrodialysis.

Discussion of the Background

The amino acid methionine is currently industrially produced worldwide in large amounts and is of considerable commercial importance. Methionine is employed in many fields, such as pharmaceutical, health and fitness products, but particularly as feedstuff additive in many feedstuffs for various livestock. On an industrial scale, methionine is produced chemically via the Bucherer-Bergs reaction, which is a variant of the Strecker synthesis. Here, the starting substances 3-methylmercaptopropanal (prepared from 2-propenal and methylmercaptan), hydrocyanic acid (hydrogen cyanide), ammonia and carbon dioxide are reacted to give 5-(2-methylmercaptoethyl)hydantoin (methionine hydantoin) and this is subsequently hydrolysed by alkali to the alkali metal methioninate (e.g. potassium methioninate) using alkali metal hydroxide and/or alkali metal carbonate and alkali metal hydrogen carbonate, for example potassium hydroxide and/or potassium carbonate and potassium hydrogen carbonate. Methionine is finally liberated from its alkali metal salt, preferably its potassium salt, by treatment with carbon dioxide, which may be filtered off as a precipitate from the mother liquor containing alkali metal carbonate and alkali metal hydrogen carbonate (e.g. potassium carbonate and potassium hydrogen carbonate) (U.S. Pat. No. 5,770, 769). The ammonia, alkali metal carbonate and alkali metal hydrogen carbonate reagents (e.g. potassium carbonate and potassium hydrogen carbonate) and also carbon dioxide are generally recycled in industrial methionine production. In time, the alkali metal salt (e.g. potassium salt) present in the process solution becomes inactivated in the form of neutral alkali metal formate (e.g. potassium formate). Alkali metal formate (e.g. potassium formate) forms from the residues of hydrocyanic acid and alkali metal salts from the hydantoin hydrolysis present in the methionine hydantoin solution (WO2013030068A2). Further by-products are, inter alia, the dipeptide methionylmethionine ("met-met", EP1564208 A1), acetate and 2-hydroxy-4-methylmercaptobutanoic acid, the hydroxy analogue of methionine (MHA). It is necessary, therefore, to continuously exchange a portion of the aqueous process solution of this hydantoin hydrolysis circuit with fresh aqueous alkali metal hydroxide solution (e.g. potassium hydroxide solution). In general, the excessive enrichment of by-products in the hydantoin hydrolysis circuit must be avoided since otherwise disruptions in methionine crystal formation occur.

A typical process solution in the hydantoin hydrolysis circuit comprises the following constituents: about 10 to 16 wt % alkali metal in the form of alkali metal salts, 5 to 8 wt % methionine, 3 to 5 wt % methionylmethionine, 0.7 to 1.1 wt % formate and 0.2 to 0.3 wt % acetate. A typical purge solution comprises the following constituents: about 2 to 6 wt % methionine, 4 to 8 wt % methionylmethionine, 6 to 14 wt % alkali metal in the form of alkali metal salts, 1 to 1.7 wt % formate and 0.3 to 0.5 wt % acetate.

Since the exchanged process solution (purge), besides approx. 3 wt % inactivated alkali metal salt (e.g. potassium salt), still comprises approx. 7-8 wt % active alkali metal salt and also methionine as further material of value, this procedure is undesirable from either an economic or from an ecological point of view.

Electrodialysis is a known method for processing wastewaters or for desalinating water. Electrodialysis is understood to mean a process in which ionogenic constituents of an aqueous solution are removed by means of an ion exchange membrane and an electrical potential difference. A further field of use of electrodialysis is, for example, the separation of amino acids having different isoelectric points in electrodialysis cells, the chambers of which are separated from one another by anion and cation exchange membranes, at different pH values under the influence of the electric field (H. Strathmann and H. Chmiel, Chem. Ing. Tech, 56 (1984) No. 3, 214-220).

Perry and Kedem (U.S. Pat. No. 4,238,307 and DE 29 07 450 A1) propose an electrodialysis method by which L-amino acids can be separated from derivatized D-enantiomers thereof in aqueous solution, for example L-methionine from N-acetyl-D-methionine, by virtue of their different isoelectric points. Koberstein and Lehmann (DE 36 03 986 A1) disclose an electrodialysis method for processing the solution of the racemate resolution of an N-acetyl-D,L-aminocarboxylic acid, in the presence of an L-amino acid cyclase, which remains after removal of the enzyme.

Bachot and Grosbois (U.S. Pat. No. 4,454,012) disclose a method for obtaining free crystalline methionine from its alkali metal salt in aqueous alkali metal salt-containing process solution, using an electrodialysis unit and with recovery of alkali metal hydroxide. A method for removing formate, acetate and other undesired anions from the process solution is not disclosed.

CN105671587A discloses a method for preparing methionine by saponification of methionine hydantoin, in which, by means of electrodialysis, the resulting methionine alkali metal salt and alkali metal carbonate are converted to methionine, alkali metal hydroxide and carbon dioxide and separated. In this method, methionine hydantoin is hydrolyzed in a process solution comprising alkali metal carbonate to the methionine alkali metal salt, and methionine and carbon dioxide is released in the weakly acidic medium by repeated treatment in an electrodialysis system comprising bipolar membranes and is separated from the process solution. Methionine is obtained by concentrating and crystallization. Alkali metal carbonate and carbon dioxide are recovered. Methods for removing formate, acetate and other undesired anions from the process solution are likewise not disclosed.

CN106349131A likewise discloses a method for preparing methionine, in which the methionine hydantoin is hydrolyzed with sodium hydroxide to the methionine sodium salt and the methionine is released using sulfuric acid. In this case, the concentration of sodium sulfate in the reused process solution is significantly reduced by using an electrodialysis unit.

CN106432020A discloses a method for preparing methionine, wherein
a) the methionine hydantoin is saponified with a basic potassium compound to yield a process solution comprising methionine potassium salt and potassium hydrogencarbonate,
b) the process solution obtained in step a) is neutralized with carbon dioxide and the crystallized methionine is separated from the process solution resulting in a process solution comprising potassium hydrogencarbonate and few amounts of methionine,
c) the process solution obtained in step b) comprising potassium hydrogencarbonate and few amounts of methionine is filtrated and subjected to an electrodialysis with homogenous membranes until the concentration of potassium hydrogencarbonate in the diluate of the electrodialysis with homogenous membranes is lower than 3-7% by weight, and
d) the electrodialyzed process solution obtained in step c) is subjected to a further electrodialysis with heterogeneous membranes until the concentration of potassium hydrogencarbonate in the diluate of the electrodialysis with heterogeneous membranes is lower than 0.1% by weight.

The methionine containing process solution obtained in step d) is then evaporated to obtain methionine. The potassium hydrogencarbonate obtained from the diluates (cf. steps c) and d)) is (concentrated by evaporation of the diluates at 120° C.) and recycled to the saponification step a). CN106432020A discloses the removal of potassium hydrogencarbonate from the methionine containing process solution of the hydantoin hydrolysis circuit by electrodialysis and its reuse for the hydrolysis of methionine hydantoin. However, CN106432020A does not disclose a method for removing formate, acetate and other undesired anions from the process solution of the hydantoin hydrolysis circuit whereby methionine, its potassium salt and potassium hydrogencarbonate remain in the process solution.

SUMMARY OF THE INVENTION

The object of the present invention is to provide a process for preparing methionine, which comprises the step of hydrolysis of 5-(2-methylmercaptoethyl)hydantoin (methionine hydantoin) in an alkaline process solution, the release of methionine from the alkali metal methioninate formed and the recycling of the alkaline process solution to the hydrolysis step after removal of methionine in which, by suitable measures, the concentrations of by-products, including formate and other anions of organic acids, are lowered such that the amount of process solution to be exchanged (purge) is reduced.

The object is achieved by a process for preparing methionine, comprising the alkaline hydrolysis of 5-(2-methylmercaptoethyl)hydantoin (methionine hydantoin) in an aqueous process solution containing alkali metal hydroxide and/or alkali metal carbonate and/or alkali metal hydrogen carbonate to give the methionine alkali metal salt and also the precipitation of methionine by neutralization with carbon dioxide, separation of the methionine from the process solution, concentration of the process solution and reuse of this process solution for the alkaline hydrolysis of the methionine hydantoin fed again to the process solution, characterized in that by-products comprising formate and other anions of organic acids containing 1 to 5 carbon atoms are removed from the process solution by electrodialysis, wherein methionine and/or alkali metal salts thereof essentially remain in the process solution and wherein an electrodialysis cell in each case comprises at least two chambers and one of these chambers is the anode compartment, which is bordered by an ion-selective anion exchange membrane and an anode, and the pH in the anode compartment is from 5.8 to 8.0.

BRIEF DESCRIPTION OF THE DRAWINGS

FIG. 4 shows the pH and voltage profile.

DETAILED DESCRIPTION OF THE INVENTION

Figure 1:
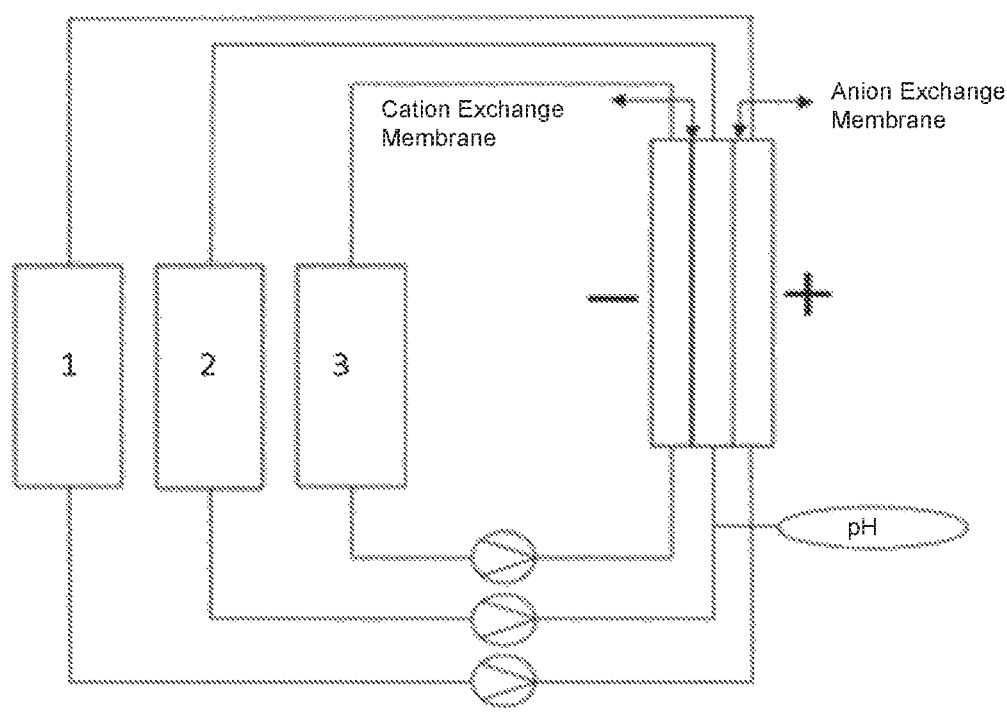
FIG. 1 schematically illustrates an electrodialysis cell.

In this process, the anions of organic acids containing 1 to 5 carbon atoms preferably comprise acetate and 2-hydroxy-4-methylmercaptobutanoate (MHA).

The current density in each case in an electrodialysis cell is preferably in a range of inclusive 1.0 to inclusive 200 A/m$^2$.

In the process according to the present invention, in each case an electrodialysis cell comprises three chambers, wherein one chamber is the cathode compartment which is bordered by a cation exchange membrane and a cathode. Optionally in each case, an electrodialysis cell may also comprise only two chambers, wherein one of the two chambers is the anode compartment and the other chamber is the cathode compartment, which is bordered by the ion-selective anion exchange membrane and an anode.

In the process according to the present invention, the electrodialysis is preferably conducted in at least two electrodialysis cells which are separated from one another in each case by means of a bipolar electrode.

In a particular configuration of the process according to the present invention, the pH in the anode compartment is adjusted by partly feeding the aqueous alkali metal hydroxide solution formed in the cathode compartment. Incidentally, the aqueous alkali metal hydroxide solution formed in the cathode compartment is fed again to the process solution.

The alkali metal in the alkali metal salts of the process solution is preferably potassium or optionally potassium and sodium.

EXAMPLES

Experimental Setup

The electrodialysis cell used in the following examples consisted of three chambers. Potassium hydrogen carbonate was initially charged in the anolyte chamber. Potassium hydroxide was initially charged in the cathode chamber. In the middle chamber, the process solution was initially charged which comprised, inter alia, methionine. The circuits were separated by ion exchange membranes and were perfused with the respective solution. Process solution circuit and anolyte circuit were separated by an anion exchange membrane and a cation exchange membrane was located between the process solution circuit and catholyte circuit. The electrolysis cell was connected to three circuit vessels which served as reservoir for the solutions. The electrodialysis cell was charged with direct current from a power unit. In the anolyte circuit the pH was monitored, which may not fall below pH 5.8, and this was maintained constant by metered addition of KOH. The conductivity of the 3 solutions was recorded in parallel.

Technical Data for the Electrodialysis Cell Used Having 3 Chambers
   Anode: dimensionally stable anode
   Cathode: Steel
   Anion exchange membrane: Tokuyama Soda AMX
   Cation exchange membrane: Tokuyama Soda CMX
   Electrode spacing: 1.5 mm
   Spacer: PVC
   Electrode area: 200 cm$^2$ Procedure 2 or 5 kg (see examples) of process solution were initially charged in the salt circuit. 2 kg of a 5% by weight KOH solution were initially charged in the catholyte and 2 kg of a 3% by weight potassium formate solution were initially charged in the anolyte. The centrifugal pumps were switched on and the pressure in the electrodialysis was adjusted by throttling the pumps. The pressure differential between the electrodialysis chambers was adjusted to less than 0.2 bar. The flow rates in the anolyte chamber and in the catholyte chamber were higher since these were used as electrode rinse. The maximum pressure in the chambers was 0.8 bar. The circuit vessels of the anolyte and catholyte were blanketed with nitrogen. The power unit was switched on to set a current density of 160 A/m$^2$. The power unit was operated galvanostatically.

Example 1

Figure 2:
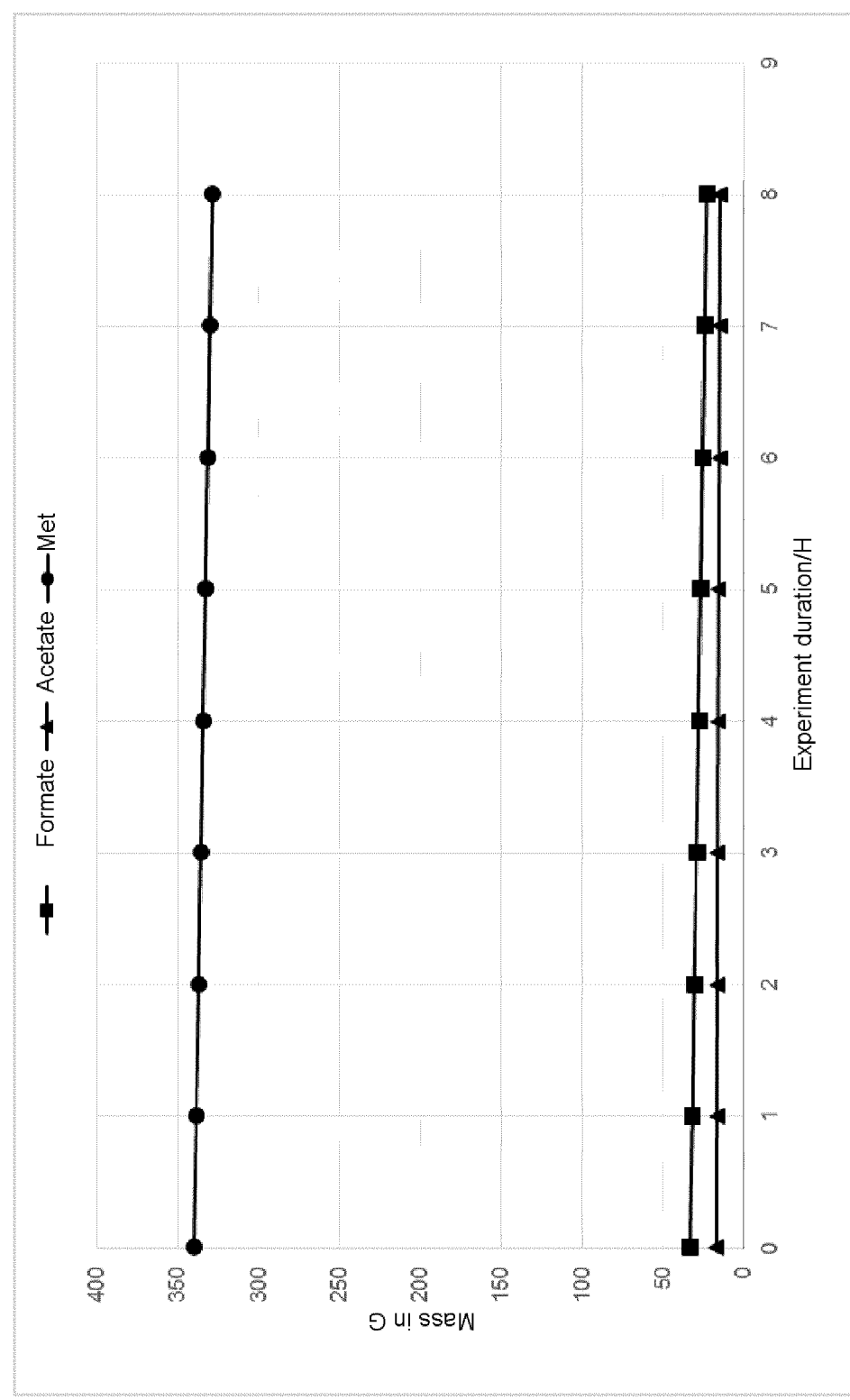
FIG. 2 graphs a concentration profile during electrolysis for Example 1.

5 kg of process solution having the composition specified in Table 1 were initially charged and electrodialyzed for 8 hours. The pH of the anolyte was maintained at pH 7 by addition of KOH from the catholyte. The concentration profile of the individual components during the electrodialysis is presented in Table 2 and in FIG. 2.

Example 2

Figure 4:
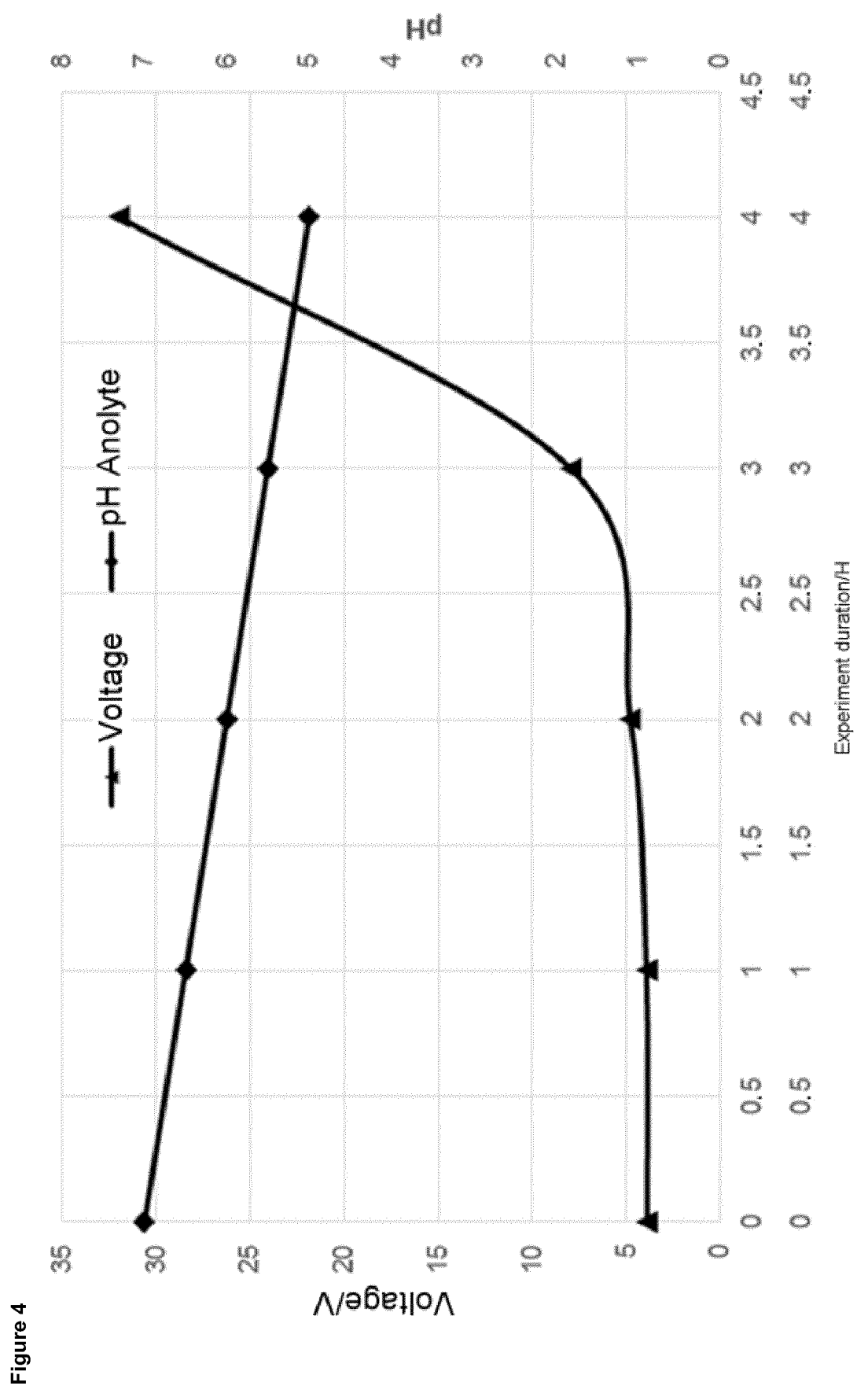

5 kg of process solution having the composition specified in Table 3 were initially charged and electrodialyzed for 8 hours. The pH of the anolyte was not regulated. The concentration profile of the individual components and the change of pH during the electrodialysis is presented in Table 4 and in FIG. 3. FIG. 4 shows the pH and voltage profile.

Figure 3:
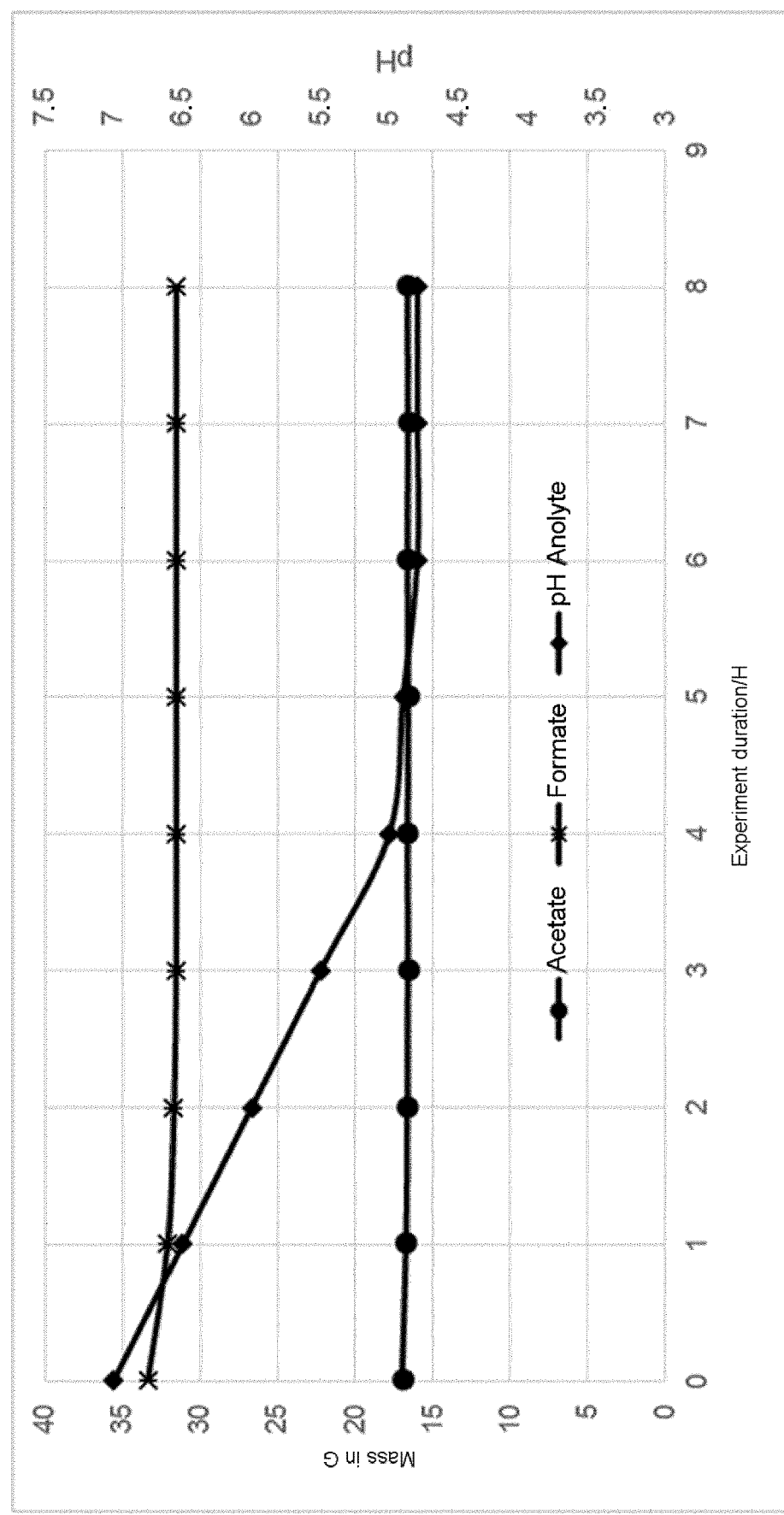
FIG. 3 graphs the concentration profile during electrolysis for Example 2.

If the pH in the anolyte falls below 6, the anion exchange membrane is blocked. The voltage increases rapidly, the removal collapses since current is no longer flowing (FIGS. 3 and 4).

TABLE 1

(Example 1)
Starting composition in g of the 5 kg of process solution

| Formate | Acetate | MHA | Met-Met | Potassium | Methionine |
|---|---|---|---|---|---|
| 33.35 | 16.97 | 29.73 | 10.71 | 630 | 340 |

TABLE 2

(Example 1)

| Time | Absolute amounts in g in the process solution | | | | | |
|---|---|---|---|---|---|---|
| h | Formate | Acetate | MHA | Met-Met | Potassium | Methionine |
| 0 | 33.35 | 16.97 | 29.72 | 10.71 | 630 | 340 |
| 1 | 32.07 | 16.71 | 29.70 | 10.63 | 627.15 | 338.59 |
| 2 | 30.79 | 16.46 | 29.67 | 10.55 | 624.31 | 337.18 |
| 3 | 29.51 | 16.20 | 29.64 | 10.48 | 621.46 | 335.77 |
| 4 | 28.23 | 15.95 | 29.61 | 10.40 | 618.62 | 334.37 |
| 5 | 26.96 | 15.70 | 29.58 | 10.32 | 615.77 | 332.96 |
| 6 | 25.68 | 15.44 | 29.56 | 10.24 | 612.93 | 331.55 |
| 7 | 24.40 | 15.19 | 29.53 | 10.16 | 610.08 | 330.14 |
| 8 | 23.12 | 14.94 | 29.50 | 10.08 | 607.24 | 328.73 |

TABLE 3

(Example 2)
Starting composition in g of the 5 kg of process solution

| Formate | Acetate | MHA | Met-Met | Potassium | Methionine |
|---|---|---|---|---|---|
| 33.35 | 16.97 | 29.73 | 10.71 | 630 | 340 |

TABLE 4

(Example 2)

| Time | Absolute amounts in g in the process solution | | | | | | pH of | Voltage |
|---|---|---|---|---|---|---|---|---|
| h | Formate | Acetate | MHA | Met-Met | Potassium | Methionine | anolyte | V |
| 0 | 33.35 | 16.97 | 29.73 | 10.7125 | 630 | 340 | 7 | 3.9 |
| 1 | 32.07 | 16.71 | 29.70 | 10.63 | 627.15 | 338.59 | 6.5 | 3.95 |
| 2 | 31.69 | 16.64 | 29.69 | 10.61 | 626.30 | 338.17 | 6 | 4.8 |
| 3 | 31.56 | 16.61 | 29.69 | 10.60 | 626.02 | 338.03 | 5.5 | 8.0 |
| 4 | 31.55 | 16.62 | 29.66 | 10.58 | 626.02 | 338.00 | 5 | 32.00 |
| 5 | 31.55 | 16.60 | 29.66 | 10.56 | 626.00 | 338.00 | 4.9 | 32.00 |
| 6 | 31.55 | 16.62 | 29.66 | 10.57 | 626.02 | 338.00 | 4.8 | 32.00 |
| 7 | 31.55 | 16.61 | 29.66 | 10.56 | 626.01 | 337.90 | 4.8 | 32.00 |
| 8 | 31.54 | 16.62 | 29.61 | 10.55 | 625.91 | 338.02 | 4.8 | 32.00 |

The invention claimed is:

1. A process for preparing methionine, comprising:
   conducting alkaline hydrolysis of 5-(2-methylmercaptoethyl)hydantoin in an aqueous process solution containing potassium hydroxide, and/or potassium carbonate, and/or potassium hydrogen carbonate to give a methionine potassium salt, precipitating methionine from a neutralized aqueous processing solution by neutralization with carbon dioxide,
separating the methionine from the neutralized aqueous process solution,
concentrating the neutralized aqueous process solution from which methionine has been removed, and
recycling the concentrated aqueous process solution to the alkaline hydrolysis of the 5-(2-methylmercaptoethyl) hydantoin step,
wherein by-products, comprising formate and other anions of organic acids containing 1 to 5 carbon atoms, are removed between processing steps and/or during a processing step by electrodialysis in at least one electrodialysis cell,
wherein a larger percentage of methionine and/or potassium salts thereof and potassium hydrogen carbonate remain during said electrodialysis relative to a percentage of formate and other anions of organic acid containing 1 to 5 carbon atoms which remains, and
wherein the electrodialysis cell comprises at least two chambers and one of the at least two chambers is an anode compartment, which is bordered by an anion exchange membrane and an anode, and the pH in the anode compartment is from 5.8 to 8.0.

2. The process according to claim 1, in which the current density in the electrodialysis cell is in a range from 1.0 to 200 A/m$^2$, inclusive.

3. The process according to claim 1, in which the electrodialysis cell comprises three chambers, wherein one chamber is a cathode compartment which is bordered by a cation exchange membrane and a cathode.

4. The process according to claim 1, in which the electrodialysis cell comprises two chambers and one of the two chambers is the anode compartment and the other chamber is a cathode compartment, wherein the cathode compartment is bordered by an anion exchange membrane and a cathode.

5. The process according to claim 1, wherein the electrodialysis is conducted in at least two electrodialysis cells, which are separated from one another by a bipolar electrode.

6. The process according to claim 1, wherein an aqueous potassium hydroxide solution is formed in a cathode compartment and is partially fed into the anode compartment to adjust the pH to from 5.8 to 8.0.

7. The process according to claim 1, wherein an aqueous potassium hydroxide solution is formed in a cathode compartment and is partially fed to the aqueous process solution for conducting alkaline hydrolysis.

* * * * *